United States Patent

Sedelmeier et al.

[11] 4,436,903
[45] Mar. 13, 1984

[54] PROCESS FOR THE PRODUCTION OF 7 β-SUBSTITUTED-3-UNSUBSTITUTED-3-CEPHEM-4-CARBOXYLIC ACID COMPOUNDS

[75] Inventors: Gottfried Sedelmeier, Ehrenkirchen-Norsingen, Fed. Rep. of Germany; Riccardo Scartazzini, Basel, Switzerland

[73] Assignee: Ciba-Geigy Corporation, Ardsley, N.Y.

[21] Appl. No.: 329,916

[22] Filed: Dec. 11, 1981

[30] Foreign Application Priority Data

Dec. 22, 1980 [CH] Switzerland ............... 9468/80

[51] Int. Cl.³ .................................. C07D 501/04
[52] U.S. Cl. .................................. 544/016; 544/22; 424/246
[58] Field of Search ............... 544/16, 21, 22, 26, 544/27, 28; 424/246

[56] References Cited

U.S. PATENT DOCUMENTS 4,001,226 1/1977 Spry ........................ 544/16
4,013,651 3/1977 Slitzer ...................... 544/22
4,246,405 1/1981 Takaya et al. ............... 544/16

*Primary Examiner*—Nicholas S. Rizzo
*Attorney, Agent, or Firm*—Irving N. Feit

[57] ABSTRACT

The invention relates to a novel advantageous process for the production of compounds of the formula

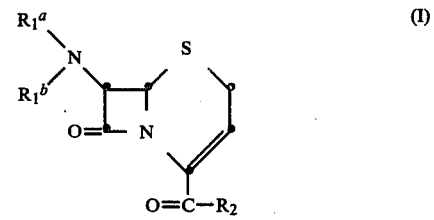

wherein n is 1, $R_1{}^a$ is hydrogen or an amino protective group $R_1{}^A$, $R_1{}^b$ is hydrogen or an acyl group Ac, or $R_1{}^a$ and $R_1{}^b$ together are a bivalent amino protective group, $R_2$ is hydroxyl or a radical which, together with the carbonyl grouping —C(=O)—, forms a protected carboxyl group, and the group of the formula —N($R_3{}^a$)($R_3{}^b$) is a secondary or tertiary amino group, or a salt thereof with salt-forming groups. The process comprises reaction of the corresponding 3-amino compounds with borohydrides in the presence of acids.

19 Claims, No Drawings

PROCESS FOR THE PRODUCTION OF 7 β-SUBSTITUTED-3-UNSUBSTITUTED-3-CEPHEM-4-CARBOXYLIC ACID COMPOUNDS

The present invention relates to a novel advantageous process for the production of 7β-substituted-3-unsubstituted-3-cephem-4-carboxylic acid compounds which are valuable antibiotic compounds or useful intermediates for obtaining antibiotic 7β-substituted-3-cephem-3-unsubstituted 4-carboxylic acid compounds. The invention also relates to the novel 1-oxides of 7β-substituted-3-amino-3-cephem-4-carboxylic acid compounds and also to processes for obtaining these compounds. In particular, the invention relates to a process for the production of 7β-substituted-3-unsubstituted-3-cephem-4-carboxylic acid compounds, which comprises reacting 7β-substituted-3-amino-3-cephem-4-carboxylic acid compounds with suitable borohydrides, in the presence of an acid reagent.

The preparation of 7β-substituted-3-cephem-3-unsubstituted-4-carboxylic acid compounds from 7β-substituted-3-amino-4-carboxylic acid compounds by reaction with diborane and subsequent acidification, is described in German Offenlegungsschrift No. 26 20 308.

The present invention provides a process for the production of 7β-amino-3-cephem-4-carboxylic acid compounds of the formula

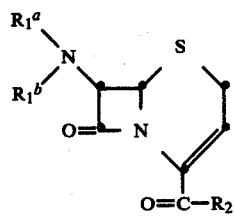
(I)

wherein $R_1{}^a$ is hydrogen or an amino protective group $R_1{}^A$, $R_1{}^b$ is hydrogen or an acyl group Ac, or $R_1{}^a$ and $R_1{}^b$ together are a bivalent amino protective group, and $R_2$ is hydroxy or a radical which, together with the carbonyl grouping —(C=O)—, forms a protected carboxyl group, and salts of compounds of the formula I with salt-forming groups, which process comprises reacting a compound of the formula

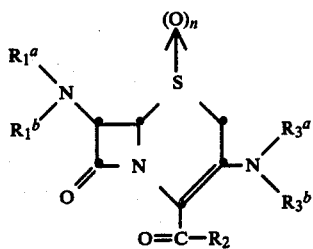
(II)

wherein n is 0 or 1, $R_1{}^a$, $R_1{}^b$ and $R_2$ are as defined for formula I, and the group of the formula —N($R_3{}^a$)($R_3{}^b$) is a secondary or tertiary amino group, or a salt thereof, with a suitable boron hydride in the presence of an acid reagent, and, if desired, in a manner known per se, converting a resultant compound of the formula I into another compound of the formula I, and/or converting protected functional groups in a compound of the formula I into the free functional groups, and/or converting a resultant salt into the free compound or into another salt, and/or converting a resultant free compound containing a salt-forming group into a salt, and/or separating a resultant mixture of isomeric compounds of the formula I into the individual isomers.

In compounds of the formula II, wherein n is 1, the corresponding 1-oxide compound is in the α- or β-form.

Throughout this specification, the term "lower" used in connection with the definitions of substituents or compounds, for example to qualify groups such as lower alkyl, lower alkylene, lower alkoxy, lower alkanoyl and the like, will be understood as meaning that, unless expressly indicated to the contrary, the groups in question contain up to 7, preferably up to 4, carbon atoms.

The functional groups present in compounds of the formula I or II, especially carboxyl, amino, hydroxyl, hydroxyimino and sulfo groups, can be protected by those protective groups which are employed in penicillin, cephalosporin and peptide chemistry. Such protective groups are easily removable, i.e. without unwanted side-reactions taking place, for example by solvolysis, reduction, photolysis or also under physiological conditions.

Protective groups of this kind and their removal are described e.g. in "Protective Groups in Organic Chemistry", Plenum Press, London, New York, 1973, and in "The Peptides", Vol. I, Schröder and Lübke, Academic Press, London, New York 1965, as well as in Houben-Weyl, "Methoden der organischen Chemie", 4th Edition, Vol. 15/1, Georg Thieme Verlag, Stuttgart, 1974.

In the starting material of the formula II and in the product of the formula I, the groups $R_1{}^A$, $R_1{}^b$, Ac and $R_2$ have the following meanings. An amino protective group $R_1{}^A$ is a group which can be replaced by hydrogen, in particular an acyl group Ac, and is also a triarylmethyl group as well as an organic silyl or stannyl group. An acyl group Ac, which can also be the group $R_1{}^b$, is in particular the acyl group of an organic carboxylic acid containing up to 18, preferably up to 10, carbon atoms, and is, in particular, the acyl group of an unsubstituted or substituted aliphatic, cycloaliphatic, cycloaliphatic-aliphatic, aromatic, araliphatic, heterocyclic or heterocyclic-aliphatic carboxylic acid. The acyl group Ac is, in particular, an acyl group of an organic carboxylic acid which is contained in an N-acyl derivative of a 6-amino-penam-3-carboxylic acid or 7-amino-3-cephem-4-carboxylic acid compound, which derivative occurs naturally or is obtainable by biosynthesis, semi-synthesis or total synthesis, and which preferably has pharmacological properties.

Such an acyl group Ac is, in particular, a group of the formula

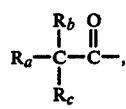
(IA)

wherein (1) $R_a$ is an unsubstituted or substituted carbocyclic aryl radical, for example phenyl, an unsubstituted or substituted, preferably unsaturated, cycloaliphatic hydrocarbon radical, for example cyclohexadienyl or cyclohexenyl, or an unsubstituted or substituted heterocyclic aryl radical, for example thienyl, furyl or thiazolyl; $R_b$ is hydrogen; and $R_c$ is hydrogen or unsubstituted or substituted, preferably protected, hydroxy, amino, carboxyl or sulfo; or wherein (2) $R_a$ is free or protected ω-amino-ω-carboxy-lower alkyl, for example ω-amino-ω-carboxypropyl, cyano, etherified hydroxy or mercapto, for example unsubstituted or substituted phenyloxy, phenylthio, or pyridylthio, or an unsubstituted or substituted, unsaturated heterocyclic radical bound through a ring nitrogen atom, for example tetrazolyl; and $R_b$ and $R_c$ are hydrogen.

Cyclohexadienyl is preferably 1,4-cyclohexadienyl, and cyclohexenyl is preferably 1-cyclohexenyl.

Thienyl is preferably 2-thienyl and also 3-thienyl. Furyl is preferably 2-furyl, and thiazolyl is preferably 4-thiazolyl. Thiadiazolyl is preferably 1,2,4-thiadiazolyl and pyridylthio is e.g. 4-pyridylthio. Tetrazolyl is e.g. 1-tetrazolyl.

Substituents of a phenyl and phenoxy radical $R_a$ can be present in any position at the phenyl ring and comprise aliphatic hydrocarbon radicals, such as unsubstituted or substituted lower alkyl, e.g. protected aminomethyl, free or functionally modified hydroxy, such as etherified or esterified hydroxy, or unsubstituted or substituted, preferably protected, amino, e.g. acylamino; or nitro which, for example, in the phenoxy group, can be in the 2-position.

Substituents of a cyclohexadienyl or cyclohexenyl radical as well as of a thienyl or furyl radical $R_a$, are e.g. unsubstituted or substituted lower alkyl, e.g. unsubstituted or substituted, for example protected, aminomethyl. A substituent of this type, especially free or protected aminomethyl, is preferably in the 2-position of a 1,4-cyclohexadienyl or 1-cyclohexenyl radical or in the 5-position of a 2-thienyl or 2-furyl radical. Substituted thiazolyl is preferably 2-amino-4-thiazolyl, wherein the amino groups are free or protected or substituted by lower alkyl, especially $C_1-C_4$ lower alkyl, for example methyl, ethyl, propyl, isopropyl, butyl or tert-butyl.

Free or protected aminomethyl is preferably aminomethyl which is unsubstituted or substituted by lower alkyl, and is e.g. methylaminomethyl. Etherified hydroxy is e.g. lower alkoxy, such as methoxy, and esterified hydroxy is e.g. lower alkanoyloxy, such as acetoxy, aroyloxy, e.g. benzoyloxy, carbamoyloxy or halogen, e.g. chlorine. Unsubstituted or substituted amino is e.g. amino substituted by lower alkyl, e.g. methylamino, or lower alkylsulfonylamino, e.g. methylsulfonylamino.

Protected hydroxyl, amino, carboxyl or sulfo groups in acyl groups Ac in formula IA are those groups which are customary in penicillin and cephalosporin chemistry and which can readily be converted into free hydroxyl, amino, carboxyl or sulfo groups without the cephem structure being destroyed or other undesired side reactions occurring.

Amino groups can be protected e.g. by acyl groups, such an acyl group being especially an acyl group of a hemiester of carbonic acid which can be split off by reduction, for example by treatment with a chemical reducing agent or with catalytically activated hydrogen, or by solvolysis, for example by treatment with a suitable acid, and also by irradiation. A protected amino group is lower alkoxycarbonyl which is preferably polybranched at the first carbon atom of the esterifying group and/or substituted by aryl, e.g. phenyl or biphenyl which is unsubstituted or substituted by lower alkoxy, e.g. methoxy and/or by nitro, or by arylcarbonyl, e.g. benzoyl, and is e.g. tert-butoxycarbonyl, tert-pentyloxycarbonyl, diphenylmethoxycarbonyl, 1-(4-biphenylyl)-1-methylethoxycarbonyl, benzyloxycarbonyl, 4-nitrobenzyloxycarbonyl, 2-nitro-4,5-dimethoxybenzyloxycarbonyl or phenacyloxycarbonyl, or is lower alkoxycarbonyl substituted at the second carbon atom of the esterifying group by halogen, e.g. 2,2,2-trichloroethoxycarbonyl or 2-iodoethoxycarbonyl, or is a group that can be converted into the latter, e.g. 2-chloroethoxycarbonyl or 2-bromoethoxycarbonyl, or is also polycyclic cycloalkoxycarbonyl, e.g. adamantyloxycarbonyl.

An amino group can also be protected by arylmethyl, such as polyarylmethyl, e.g. by trityl; a 2-carbonylvinyl grouping, e.g. a 1-lower alkoxycarbonyl-1-propen-2-yl group, e.g. 1-methoxycarbonyl-1-propen-2-yl; by an arylthio or aryl-lower alkylthio group, e.g. 2-nitrophenylthio or pentachlorophenylthio, by tritylthio or an arylsulfonyl group; also by an organic silyl or stannyl group, e.g. a silyl or stannyl group substituted by lower alkyl, halo-lower alkyl, cycloalkyl, phenyl or phenyl-lower alkyl, or by functionally modified groups, such as lower alkoxy, e.g. methoxy, or by halogen, e.g. chlorine, for example by tri-lower alkylsilyl, e.g. trimethylsilyl, halo-lower alkoxy-lower alkylsilyl, e.g. chloromethoxymethylsilyl, or also tri-lower alkylstannyl, e.g. tri-n-butylstannyl.

Hydroxyl protective groups are e.g. acyl groups, in particular one of the acyl groups of carbonic acid hemiesters mentioned in connection with a protected amino group, or are organic silyl or stannyl radicals, and also easily removable 2-oxa- or 2-thia-aliphatic or 2-oxa- or 2-thia-cycloaliphatic hydrocarbon radicals. Hydroxyl protective groups are, in particular, 1-lower alkoxy-lower alkyl or 1-lower alkylthio-lower alkyl, e.g. 1-methoxyethyl, 1-ethoxyethyl, 1-methylthioethyl or 1-ethylthioethyl, or 2-oxy- or 2-thia-cyclo-lower alkyl containing from 5 to 7 ring atoms, e.g. 2-tetrahydrofuryl or 2-tetrahydropyranyl or corresponding thia analogs, as well as unsubstituted or substituted, easily removable α-phenyl-lower alkyl radicals, e.g. unsubstituted or substituted benzyl or diphenylmethyl, suitable substituents of the phenyl radicals being e.g. halogen such as chlorine, lower alkoxy such as methoxy, and/or nitro.

A protected carboxyl or sulfo group is preferably a carboxyl or sulfo groups esterified with an aliphatic, cycloaliphatic, cycloaliphatic-aliphatic, aromatic or araliphatic alcohol, such as a lower alkanol, or with a silyl or stannyl group, such as tri-lower alkylsilyl. In a carboxyl or sulfo group, the hydroxyl group can be etherified e.g. in the same manner as the hydroxyl group in an esterified carboxyl group of the formula —C(=O)—$R_2$.

An amino group protected by an amino-protective group $R_1^A$ can also be e.g. an amino group protected by the acyl group of a carbonic acid hemiester, a 2-carbonylvinyl, arylthio or aryl-lower alkylthio group, or an arylsulfonyl group, a triarylmethyl radical, or an organic silyl or stannyl group. Such a protective group can be the same as that of a correspondingly protected amino group in an acyl radical of the formula IA.

A bivalent amino-protective group formed by the radicals $R_1^a$ and $R_1^b$ together is, in particular, the bivalent acyl radical of an organic dicarboxylic acid, preferably containing up to 18 carbon atoms, more especially the diacyl group of an aliphatic or aromatic dicarboxylic acid, e.g. the acyl group of a lower alkanedicarboxylic acid or lower alkenedicarboxylic acid, such as succinyl, or of an o-arylenedicarboxylic acid, such as phthaloyl, or is also the acyl group or an α-aminoacetic acid preferably substituted in the α-position, e.g. containing an aromatic or heterocyclic radical, the amino group of which is attached to the nitrogen atom through a methylene radical which is preferably substituted, for example which contains two lower alkyl groups, such as methyl groups, for example a 1-oxo-3-aza-1,4-butylene radical which is preferably substituted in the 2-position, e.g. containing unsubstituted or substituted phenyl or thienyl, and unsubstituted or mono- or disubstituted in the 4-position by lower alkyl such as methyl, for example 4,4-dimethyl-2-phenyl-1-oxo-3-aza-1,4-butylene.

The groups $R_1{}^a$ and $R_1{}^b$ together can also be an organic ylidene group, e.g. an aliphatic, cycloaliphatic, cycloaliphatic-aliphatic or araliphatic, ylidene group, preferably containing up to 18 carbon atoms.

A protected carboxyl group of the formula —C(=O)—$R_2$ is, in particular, an esterified carboxyl group, in which $R_2$ is a hydroxyl group substituted by an organic radical or an organic silyl or stannyl group. Such organic radicals, also as substituents in organic silyl or stannyl groups, are aliphatic, cycloaliphatic, cycloaliphatic-aliphatic, aromatic or araliphatic radicals, in particular unsubstituted or substituted hydrocarbon radicals of this kind, as well as heterocyclic or heterocyclic-aliphatic radicals, preferably containing up to 18 carbon atoms.

A substituted hydroxyl group $R_2$, together with the carbonyl grouping, forms a carboxyl group that can preferably readily be cleaved, for example by reduction, such as by hydrogenolysis, or by solvolysis, such as acidolysis, or by hydrolysis, and also by oxidation, or one that can readily be converted into a different functionally modified carboxyl group, such as an esterified carboxyl group that can be converted into a different esterified carboxyl group or into a hydrazinocarbonyl group. An $R_2$ group of this kind is e.g. 2-halo-lower alkoxy, the halogen preferably having an atomic weight of more than 19, for example 2,2,2-trichloroethoxy or 2-iodoethoxy, or 2-chloroethoxy or 2-bromoethoxy which can readily be converted into the latter, or 2-lower alkylsulfonyl-lower alkoxy, for example 2-methylsulfonylethoxy. The group $R_2$ is also a methoxy group polysubstituted by unsubstituted or substituted hydrocarbon radicals, especially saturated aliphatic or aromatic hydrocarbon radicals, such as lower alkyl, for example methyl, and/or phenyl, or is a methoxy group monosubstituted by an unsaturated aliphatic hydrocarbon radical such as lower alkenyl, for example 1-lower alkenyl such as vinyl, by a carbocyclic aryl group containing electron-donating substituents or by a heterocyclic group of aromatic character containing oxygen or sulfur as ring member; such as tert-lower alkoxy, for example tert-butoxy or tert-pentyloxy, unsubstituted or substituted diphenylmethoxy, for example diphenylmethoxy or 4,4'-dimethoxydiphenylmethoxy, lower alkenyloxy, especially 2-lower alkenyloxy, for example allyloxy, lower alkoxyphenyl-lower alkoxy, for example lower alkoxy-benzyloxy, such as methoxybenzyloxy (methoxy being preferably in the 3-, 4- and/or 5-position), preferably 3- or 4-methoxybenzyloxy, 3,4-dimethoxybenzyloxy, or, most preferably, nitrobenzyloxy, e.g. 4-nitrobenzyloxy, 2-nitrobenzyloxy or 4,5-dimethoxy-2-nitrobenzyloxy, as well as furfuryloxy, such as 2-furfuryloxy. $R_2$ can also be 2-oxa- or 2-thia-cycloalkoxy or 2-oxa- or 2-thia-cycloalkenyloxy containing 5 to 7 ring members, such as 2-tetrahydrofuryloxy, 2-tetrahydropyranyloxy or 2,3-dihydro-2-pyranyloxy or a corresponding thia group, or arylcarbonylmethoxy, in which aryl is preferably an unsubstituted or substituted phenyl group, e.g. phenacyloxy, or $R_2$, together with the —C(=O)— grouping, forms an activated ester group and is e.g. nitrophenoxy, such as 4-nitrophenoxy or 2,4-dinitrophenoxy, or polyhalophenoxy such as pentachlorophenoxy. $R_2$ can however, also be unbranched lower alkoxy, e.g. methoxy or ethoxy.

An organic silyloxy or stannyloxy group $R_2$ is preferably a silyloxy or stannyloxy group substituted by 1 to 3 unsubstituted or substituted hydrocarbon radicals preferably containing up to 18 carbon atoms. This group preferably contains, as substituents, aliphatic, cycloaliphatic, aromatic or araliphatic hydrocarbon radicals, unsubstituted or substituted, for example substituted by lower alkoxy, such as methoxy, or by halogen, such as chlorine, for example lower alkyl, halo-lower alkyl, cycloalkyl, phenyl or phenyl-lower alkyl, and is preferably tri-lower alkylsilyloxy, e.g. trimethylsilyloxy, halo-lower alkoxy-lower alkylsilyloxy, e.g. chloromethoxymethylsilyloxy, or tri-lower alkylstannyloxy, e.g. tri-n-butylstannyloxy.

The group $R_2$ can also be a substituted hydroxyl group which, together with the carbonyl grouping —C(=O)—, forms an esterified carboxyl group that can be cleaved under physiological conditions, especially an acyloxymethoxy group, in which acyl is e.g. the radical of an organic carboxylic acid, especially the radical of an unsubstituted or substituted lower alkanecarboxylic acid, or in which acyloxymethyl forms the radical of a lactone. Such hydroxyl groups are lower alkanoyloxymethoxy, e.g. acetoxymethoxy or pivaloyloxymethoxy, amino-lower alkanoyloxymethoxy, preferably α-amino-lower alkanoyloxymethoxy, e.g. glycyloxymethoxy, L-valyloxymethoxy, L-leucyloxymethoxy, or also phthalidyloxy.

A radical $R_2$ which, together with a —C(=O)— grouping, forms an unsubstituted or substituted hydrazinocarbonyl group, is e.g. hydrazino or 2-lower alkylhydrazino, e.g. 2-methylhydrazino.

Salts are, in particular, salts of compounds of the formula I or II which contain an acid group, e.g. a carboxyl group, and are preferably metal or ammonium salts, such as alkali metal and alkaline earth metal salts, for example sodium, potassium, magnesium or calcium salts, and also ammonium salts with ammonia or suitable organic amines. The most preferred amines for the salt formation are aliphatic, cycloaliphatic, cycloaliphatic-aliphatic and araliphatic primary, secondary or tertiary, mono-, di- or polyamines, as well as heterocyclic bases such as lower alkylamines, e.g. triethylamine, hydroxy-lower alkylamines, e.g. 2-hydroxyethylamine, di-(2-hydroxyethyl)amine or tri-(2-hydroxyethyl)amine, basic aliphatic esters of carboxylic acids, e.g. 4-aminobenzoic acid 2-diethylaminoethyl ester, lower alkyleneamines, e.g. 1-ethylpiperidine, cycloalkylamines, e.g. bicyclohexylamine, or benzylamines, e.g. N,N'-dibenzylethylenediamine; and also bases of the pyridine type, e.g. pyridine, collidine or quinoline. Compounds of the formula I or II that contain a basic group can also form acid addition salts, for example with inorganic acids, such as hydrochloric acid, sulfuric acid or phosphoric acid, or with suitable organic carboxylic or sulfonic acids, for example trifluoroacetic acid or p-toluenesulfonic acid. Compounds of the formula I or II containing an acid group and a basic group may also exist in the form of inner salts, that is to say, in zwitterionic form. 1-Oxides of compounds of the formula I or II containing salt-forming groups can likewise form salts, as described above. In a starting material of the formula II, the preferred salts are those which do not interfere with the reduction reaction.

In a starting material of the formula II, one of the substituents $R_3^a$ and $R_3^b$ in a secondary amino group —$N(R_3^a)(R_4^b)$ is hydrogen and the other is an aliphatic or cycloaliphatic hydrocarbon radical which contains about up to 18, preferably up to 12 and, most preferably, up to 7, carbon atoms. Aliphatic hydrocarbon radicals $R_3^a$ or $R_4^b$ are e.g. alkyl, preferably lower alkyl radicals, which are unsubstituted or substituted e.g. by lower alkoxy such as methoxy, lower alkylthio such as methylthio, cycloalkyl such as cyclohexyl, aryl such as phenyl, or heterocyclyl such as thienyl, and are e.g. methyl, ethyl, propyl, isopropyl, butyl, isobutyl, pentyl, hexyl, 2-ethoxyethyl, 2-methylthioethyl, cyclohexylmethyl, benzyl or thienylmethyl. Cycloaliphatic hydrocarbon radicals $R_3^a$ and $R_3^b$ are e.g. cycloalkyl radicals which are unsubstituted or substituted e.g. by lower alkyl such as methyl, lower alkoxy such as methoxy, lower alkylthio such as methylthio, cycloalkyl such as cyclohexyl, aryl such as phenyl, or heterocyclyl such as thienyl, and are e.g. cyclopropyl, cyclopentyl, cyclohexyl or cycloheptyl, unsubstituted or substituted as indicated above.

In tertiary amino groups —$N(R_3^a)(R_3^b)$, each of the substituents $R_3^a$ and $R_3^b$ is one of the indicated aliphatic or cycloaliphatic hydrocarbon radicals and can be the same or different. Both substituents $R_3^a$ and $R_3^b$ can be linked to each other through a carbon-carbon bond or through an oxygen or sulfur atom or through an unsubstituted or substituted, e.g. lower alkylated, for example methylated, nitrogen atom.

Suitable tertiary amino groups —$N(R_3^a)(R_3^b)$ are e.g. dimethylamino, diethylamino, N-methylethylamino, diisopropylamino, N-methylisopropylamino, dibutylamino, N-methylisobutylamino, dicyclopropylamino, N-methylcyclopropylamino, dicyclopentylamino, N-methylcyclopentylamino, dicyclohexylamino, N-methylcyclohexylamino, dibenzylamino, N-methylbenzylamino, N-cyclopropylamino, 1-aziridinyl, 1-pyrrolidinyl, 1-piperidinyl, 1H-2,3,4,5,6,7-hexahydroazepinyl, 4-morpholinyl, 4-thiomorpholinyl, 1-piperazinyl or 4-methyl-1-piperazinyl.

In a product of the formula I, an acyl group Ac is also a group of the formula Ia, wherein (3) $R_a$ is an unsubstituted or substituted carbocyclic aryl radical, e.g. phenyl, or an unsubstituted or substituted heterocyclic aryl radical, e.g. thienyl, furyl, thiazolyl or thiadiazolyl, and $R_b$ and $R_c$ together are preferably O-substituted hydroximino in the syn-configuration.

O-Substituted hydroximino is preferably lower alkoximino, e.g. methoximino or ethoximino, and also phenyloximino or phenyl-lower alkoximino, e.g. benzyloximino. These groups are preferably in the syn-form.

The invention relates in particular to a process for the production of compounds of the formula I, in which $R_1^a$ is hydrogen or preferably an acyl group Ac present in an N-acyl derivative of a 6β-amino-penam-3-carboxylic acid compound or a 7β-amino-3-cephem-4-carboxylic acid compound, which derivative can be obtained by fermentation (that is to say, one which is naturally occurring) or by bio-synthesis, semi-synthesis or total synthesis, e.g. an acyl group of the formula (IA) mentioned above, wherein, $R_a$, $R_b$ and $R_c$ have the preferred meanings and $R_1^b$ is hydrogen, or in which $R_1^a$ and $R_1^b$ together are a 1-oxo-3-aza-1,4-butylene radical substituted in the 2-position preferably, for example, by an aromatic or heterocyclic radical, e.g. phenyl, and in the 4-position by two lower alkyl radicals such as methyl; $R_2$ is a hydroxyl group or a hydroxyl group substituted by an organic radical or an organic silyl or stannyl group, or an unsubstituted or substituted hydrazino group, and salts of such compounds with salt-forming groups, from correspondingly substituted compounds of the formula II, and the 1-oxides or salts thereof.

In a compound of the formula I or II, or in a salt of such a compound with salt-forming groups, $R_1^a$ is preferably hydrogen or an acyl group of the formula IA, wherein (1) $R_a$ has the preferred meanings stated above and is e.g. phenyl, thienyl, furyl, cyclohexadienyl or cyclohexenyl, each unsubstituted or substituted by hydroxy, protected hydroxy, lower alkoxy, lower alkanoyloxy, carbamoyloxy, halogen, lower alkylsulfonylamino or aminomethyl, or thiazolyl or thiadiazolyl substituted by amino, lower alkylamino or protected amino; $R_b$ is hydrogen, and $R_c$ is hydrogen, free or protected hydroxy, free or protected amino or free or protected carboxyl or sulfo; or wherein (2) $R_a$ is free or protected 3-amino-3-carboxypropyl, cyano, 1-tetrazolyl, phenoxy unsubstituted or substituted in the same manner as phenyl, or 4-pyridylthio, and $R_b$ and $R_c$ are hydrogen; $R_1^b$ is hydrogen, and $R_2$ is lower alkoxy or α-polybranched lower alkoxy, e.g. methoxy or tert-butoxy, or 2-halo-lower alkoxy, e.g. 2,2,2-trichloroethoxy, 2-iodoethoxy, or 2-chloroethoxy or 2-bromoethoxy which can readily be converted thereinto, or also phenacyloxy, 1-phenyl-lower alkoxy having from 1 to 3 phenyl nuclei which are unsubstituted or substituted by lower alkoxy and/or by nitro, e.g. 4-methoxybenzyloxy, 4-nitrobenzyloxy, 2-nitro-4,5-dimethoxybenzyloxy, diphenylmethoxy, 4,4'-dimethoxydiphenylmethoxy or trityloxy, lower alkanoyloxymethoxy, e.g. acetoxymethoxy or pivaloyloxymethoxy, α-amino-lower alkanoyloxymethoxy, e.g. glycyloxymethoxy, 2-phthalidyloxy, as well as lower alkenyloxy, preferably 2-lower alkenyloxy, for example allyloxy.

In particular, $R_1^a$ in a compound of the formula II is also an acyl group Ac of the formula I, wherein (3) $R_a$ is phenyl, thienyl, furyl or thiazolyl or thiadiazolyl protected by amino, lower alkylamino or protected amino, and $R_b$ and $R_c$ together are syn-lower alkoximino.

The invention relates more particularly to a process for the production of compounds of the formula I, in which $R_1^a$ is hydrogen or an acyl group of the formula IA, wherein (1) $R_a$ is phenyl, hydroxyphenyl, e.g. 3- or 4-hydroxyphenyl, lower alkylsulfonylaminophenyl, e.g. 3-methylsulfonylaminophenyl, aminomethylphenyl, e.g. 2-aminomethylphenyl, thienyl, e.g. 2- or 3-thienyl, aminomethylthienyl, e.g. 5-aminomethyl-2-thienyl, furyl, e.g. 2-furyl, aminomethylfuryl, e.g. 5-aminomethyl-2-furyl, cyclohexadienyl, e.g. 1,4-cyclohexadienyl, aminomethyl-1,4-cyclohexadienyl, e.g. 2-aminomethyl-1,4-cyclohexadienyl, cyclohexenyl, e.g. 1-cyclohexenyl, aminomethyl-1-cyclohexenyl, e.g. 2-aminomethyl-1-cyclohexenyl, aminothiazolyl, e.g. 2-amino-4-thiazolyl, lower alkylaminothiazolyl, e.g. 2-methylamino-4-thiazolyl, aminothiadiazolyl, e.g. 5-amino-1,2,4-thiadiazolyl, or lower alkylaminothiadiazolyl, e.g., 5-methylamino-1,2,4-thiadiazolyl, in which radicals hydroxy and/or amino are unsubstituted or protected by acyl, e.g. unsubstituted or halogenated lower alkoxycarbonyl, e.g. tert-butyloxycarbonyl or 2,2,2-trichloroethoxycarbonyl; $R_b$ is hydrogen, and $R_c$ is hydrogen, amino, or protected amino such as acylamino, e.g. β- polybranched lower alkoxycarbonylamino such as tert-butoxycarbonylamino or 2-halo-lower alkoxycarbonylamino, e.g. 2,2,2-trichloroethoxycarbonylamino, 2-iodoethoxycarbonylamino or 2-bromoethoxycarbonylamino, or unsubstituted or lower alkoxy-substituted and/or nitro-substituted phenyl-lower alkoxycarbonylamino, e.g. 4-methoxybenzyloxycarbonylamino or diphenylmethoxycarbonylamino, or is hydroxy, or protected hydroxy, e.g. acyloxy such as β-polybranched lower alkoxycarbonyloxy, e.g. tert-butoxycarbonyloxy, or 2-halo-lower alkoxycarbonyloxy such as 2,2,2-trichloroethoxycarbonyloxy, 2-iodoethoxycarbonyloxy or 2-bromoethoxycarbonyloxy, or is carboxyl, free or esterified e.g. by lower alkyl, or sulfo, or wherein (2) $R_a$ is 3-amino-3-carboxypropyl, in which amino can be protected, for example in the same manner as the above amino group $R_c$, and carboxy can be protected, for example in the same manner as the 4-carboxyl group —C(=O)—$R_2$, cyano, 1-tetrazolyl, phenoxy or 4-pyridylthio, and $R_b$ and $R_c$ are hydrogen, $R_1{}^b$ is hydrogen, and $R_2$ is hydroxy, methoxy, α-poly-branched lower alkoxy, for example tert-butoxy, 2-halo-lower alkoxy, e.g. 2,2,2-trichloroethoxy, 2-iodoethoxy or 2-bromoethoxy, or diphenylmethoxy unsubstituted or substituted e.g. by lower alkoxy such as methoxy, e.g. diphenylmethoxy or 4,4'-dimethoxydiphenylmethoxy, or 4-nitrobenzyloxy, tri-lower alkylsilyloxy, e.g. trimethylsilyloxy, as well as 2-lower alkenyloxy, e.g. allyloxy, and salts thereof from correspondingly substituted compounds of the formula II, and the 1-oxides or salts thereof.

In a compound of the formula I, $R_1{}^a$ is also preferably an acyl group of the formula IA, wherein (3) $R_a$ is phenyl, thienyl, 2-furyl, 2-amino-4-thiazolyl, 2-lower alkylamino-4-thiazolyl, e.g. 2-methylamino-4-thiazolyl, 5-amino-1,2,4-thiadiazolyl or 5-lower alkylamino-1,2,4-thiadiazolyl, e.g. 5-methylamino-1,2,4-thiadiazolyl, wherein amino can be protected by acyl, e.g. by unsubstituted or halogenated lower alkoxycarbonyl, e.g. tert-butoxycarbonyl or 2,2,2-trichloroethoxycarbonyl, and $R_b$ and $R_c$ together are syn-lower alkoximino, e.g. syn-methoximino.

The invention relates more particularly to a process for the production of compounds of the formula I, wherein (1) $R_a$ is phenyl, 2- or 3-thienyl, 2- or 3-furyl, $R_b$ is hydrogen, or amino, free or protected e.g. as described above, and $R_c$ is hydrogen; or wherein (2) $R_a$ is phenoxy, and each of $R_b$ and $R_c$ is hydrogen, $R_2$ is hydroxy, an esterified hydroxyl group, e.g. lower alkoxy such as methoxy or tert-butoxy, 2-halo-lower alkoxy, e.g. 2,2,2-trichloroethoxy, nitrobenzyloxy, e.g. 4-nitrobenzyloxy, or diphenylmethoxy, and salts of such compounds with salt-forming groups from correspondingly substituted compounds of the formula II, the 1-oxides or salts thereof, as well as 1-oxides of compounds of the formula II and salts thereof with salt-forming groups.

In a compound of formula I, $R_1{}^a$ is also preferably an acyl group of the formula IA, wherein (3) $R_a$ is phenyl or 2-amino-4-thiazolyl, 2-lower alkylamino-4-thiazolyl, e.g. 2-ethylamino-4-thiazolyl, wherein amino can be protected, for example, by acyl, such as unsubstituted or halogenated lower alkoxycarbonyl, for example tert-butoxycarbonyl or 2,2,2-trichloroethoxycarbonyl, and $R_b$ and $R_c$ together are syn-lower alkoximino, for example syn-methoximino.

Suitable borohydrides for the process of the invention are e.g. complex borohydrides, e.g. complex borohydrides in salt form, e.g. metal borohydrides such as zinc borohydride, alkali metal borohydrides, for example sodium or potassium borohydride, or those complex borohydrides in which one to three hydrogen atoms are replaced by cyano or by acyloxy groups, for example by unsubstituted or halogenated alkanoyloxy groups, for example formyloxy, acetoxy, propionyloxy, palmityloxy, monochloroacetoxy or trifluoroacetoxy, or by aromatic acyloxy groups, for example benzyloxy, or by lower alkoxy, for example ethoxy or isopropoxy, or by alkyl radicals, e.g. n-propyl, n-butyl, isopropyl or sec-butyl, e.g. lithium cyanoborohydride ($LiBH_3CN$), sodium cyanoborohydride, sodium triacetyloxyborohydride [$NaBH(CH_3COO)_3$], sodium triethoxyborohydride, potassium triisopropoxyborohyride, lithium tri-sec-butylborohydride, potassium tri-sec-butylborohydride, as well as ammonium borohydrides, wherein the ammonium ion can be substituted by 1 to 4 alkyl groups, e.g. n-butyl groups, and the borohydride anion can be substituted by 1 to 3 of the above radicals, e.g. tetrabutylammonium borohydride [$(C_4H_9)_4NBH_4$] or tetrabutylammonium cyanoborohydride [$(C_4H_9)_4NBH_3CN$], or borohydride complexes with primary, secondary or tertiary amines or with diorganyl sulfides, e.g. tert-butylamine borane, dimethylamine borane, trimethylamine borane, triethylamine borane or dimethylsulfide borane. Suitable borohydrides are also monoalkyl boranes containing a branched alkyl radical of about 5 to 10 carbon atoms, e.g. "thexyl borane" [$(CH_3)_2CH-C(CH_3)_2BH$], dialkyl boranes, both alkyl moieties of which are linked to each other, e.g. "borabicyclononane" (9-BBN), prepared from cycloocta-1,5-diene and diborane. At least an equivalent amount of borohydride is used, based on the starting material of the formula II, with the preferred amount being from 1 to 10 equivalents and, where the S-oxide of the formula II is used, from 2 to 10 equivalents, if desired in portions.

Preferred complex borohydrides are e.g. alkali metal borohydride, e.g. sodium or potassium borohydride, sodium cyanoborohydride and sodium triacetyloxyborohydride. This last mentioned compound can be prepared in situ from sodium borohydride and an excess of glacial acetic acid.

Acid reagents employed in the process of the invention are strong and weak acids of the Brönstedt type, for example mineral acids, e.g. sulfuric acid or hydrochloric acid, organic acids or Lewis acids, if desired in admixture with other acids.

Organic acids employed in the process of the invention are carboxylic acids, dicarboxylic acids or sulfonic acids. Suitable organic acids are, in particular, aliphatic, cycloaliphatic or aromatic carboxylic acids, dicarboxylic acids or sulfonic acids, which can be substituted by halogen, e.g. chlorine, lower alkoxy, e.g. methoxy, hydroxy or by aryl, e.g. phenyl.

Examples of aliphatic carboxylic acids are lower alkanecarboxylic acids which may be substituted as indicated above, e.g. formic acid, acetic acid, propionic acid, butyric acid, chloroacetic acid, trifluoroacetic acid or phenylacetic acid. Examples of cycloaliphatic carboxylic acids are cyclopentane- or cyclohexanecarboxylic acids which are substituted as indicated above. Examples of carboxylic acids are benzoic acid or substituted benzoic acid, e.g. chlorobenzoic acid or methoxybenzoic acid.

Examples of aliphatic dicarboxylic acids are lower alkanedicarboxylic acids which may be substituted as indicated above, e.g. oxalic acid, malonic acid, succinic acid, glutaric acid or adipic acid.

Examples of aliphatic sulfonic acid are methanesulfonic acid or ethanesulfonic acid. Examples of aromatic sulfonic acids are arylsulfonic acids which may be substituted as indicated above, e.g. benzenesulfonic acid or p-toluenesulfonic acid.

Lewis acids employed in the process of the invention which may be used in admixture with the organic acids specified above, are non-oxidising and non-reducing and are e.g. transition metal halides, e.g. titanium(IV) chloride, zirconium(IV) chloride, nickel chloride, zinc chloride, iron(III) chloride, cobalt(III) chloride or chromium(III) chloride, or halides of the 3rd and 4th main group of the Periodic Table, e.g. aluminium trichloride, silicon tetrachloride or tin tetrachloride.

Preferred acid reagents are e.g. acetic acid, formic acid, and cobalt(II) chloride or titanium tetrachloride in admixture with acetic acid.

At least one mole of acid reagent is used per mole of compound of the formula II. It is preferred to use a large excess, if desired as solvent. Mineral acids are used in dilute form, e.g. as methanolic solution.

The reduction according to the invention is carried out either in one of the above-mentioned organic liquid acids alone or with the addition of a further solvent. Suitable additional solvents are inert solvents which do not participate in the reduction, especially polar solvents such as halogenated hydrocarbons, e.g. methylene chloride; ethers, e.g. diethyl ether; lower alkylene glycol di-lower alkyl ethers, e.g. dimethoxyethane or diethylene glycol dimethyl ether; cyclic ethers, e.g. dioxane or tetrahydrofurane; carboxamides, e.g. dimethyl formamide; or lower alkanols, e.g. methanol, ethanol or tert-butanol; or mixtures thereof. If necessary, the reaction is carried out in an inert gas atmosphere, for example an argon or nitrogen atmosphere.

The reaction temperature is in the range from $-20°$ to $80°$ C., with the preferred range being from $0°$ to $30°$ C.

It is preferred to react a compound of the formula II, e.g. 7β-phenoxyacetylamino-3-morpholino-3-cephem-4-carboxylic acid benzhydryl ester, 7β-phenoxyacetylamino-3-piperidino-3-cephem-4-carboxylic acid benzhydryl ester, 7β-benzylacetylamino-3-morpholino-3-cephem-4-carboxylic acid benzhydryl ester, 7β-[2-(2-thienyl)-acetylamino]-3-pyrrolidino-3-cephem-4-carboxylic acid p-nitrobenzyl ester 1-oxide or 7β-phenoxyacetylamino-3-pyrrolidino-3-cephem-4-carboxylic acid benzhydryl ester, with sodium or potassium borohydride, sodium cyanoborohydride and sodium triacetyloxyborohydride as complex borohydrides, in the presence of glacial acetic acid or of cobalt(II) chloride or titanium(IV) chloride, in glacial acetic acid as acid reagent and dimethyl formamide, tetrahydrofurane, ethanol, methylene chloride, xylene, toluene or ethylene glycol dimethyl ether as solvent, in the temperature range from $0°$ to about $30°$ C.

Resultant compounds of the formula I, wherein $R_1{}^a$ is an amino protective group $R_1{}^A$, $R_1{}^b$ is hydrogen or an acyl group Ac, $R_1{}^a$ and $R_1{}^b$ together are a bivalent amino protective group and $R_2$ is a radical which, together with the carbonyl grouping, forms a protected carboxyl group, can be converted into compounds of the formula I, wherein $R_1{}^a$ and $R_1{}^b$ are hydrogen and $R_2$ is hydroxyl, by deacylation and removal of the 4-carboxyl protective group by methods analogous to those described in German Offenlegungsschrift specification Nos. 1 795 868 and 1 445 615.

Resultant compounds of the formula I, wherein $R_1{}^a$ and $R_1{}^b$ are hydrogen and $R_2$ is hydroxyl or a radical which, together with the carbonyl grouping —C(=O)—, forms a protected carboxyl group, can be converted into compounds of the formula I, wherein $R_1{}^a$ is an amino protective group $R_1{}^A$, and $R_1{}^b$ is hydrogen or an acyl group Ac, or $R_1{}^a$ and $R_1{}^b$ together are a bivalent amino protective group, by methods similar to those described in German Offenlegungsschrift No. 2 151 567 and published European patent application Nos. 0008343, 0007470 and 0013762, by acylation of the 7β-amino group.

Salts of compounds of the formula I can be prepared in a manner known per se. For example, salts of such compounds with acid groups can be obtained e.g. by treatment with metal compounds such as alkali metal salts of suitable carboxylic acids, for example the sodium salt of α-ethylcaproic acid, or with ammonia or with a suitable organic amine, preferably using stoichiometric amounts or only a slight excess of the salt-forming agent. Acid addition salts of compounds of the formula I with basic groupings are obtained in customary manner, for example by treatment with an acid or a suitable anion exchange reagent. Inner salts of compounds of the formula I which contain, for example, a salt-forming amino group and a free carboxyl group, can be obtained e.g. by neutralising salts such as acid addition salts, to the isoelectric point, for example with weak bases, or by treatment with liquid ion exchangers. Salts of 1-oxides of compounds of the formula I with salt-forming groups can be prepared in similar manner.

Salts can be converted into the free compounds in conventional manner: metal and ammonium salts can be converted e.g. by treatment with suitable acids, and acid addition salts, e.g. by treatment with a suitable base.

Resultant mixtures of isomers can be separated into the individual isomers by methods known per se. Mixtures of diastereomeric isomers can be separated by fractional crystallisation, adsorption chromatography (column or thin-layer chromatography) or by other suitable separating processes. Racemates can be resolved into the antipodes in conventional manner, if desired after the introduction of suitable salt-forming groups, e.g. by preparing a mixture of diastereomeric salts with optically active salt-forming agents, separating the mixture into the diastereomeric salts, and converting the salts into the free compounds, or by fractional crystallisation from optically active solvents.

The process also comprises those embodiments in which compounds formed as intermediates are used as starting materials and the remaining process steps are carried out therewith, or the process is interrupted at any stage; furthermore, starting materials can be used in the form of derivatives or formed during the reaction.

The starting materials and reaction conditions are preferably so chosen that the compounds referred to at the outset as being particularly preferred are obtained.

The compounds of the formula II, wherein n is 1, are novel and likewise constitute an object of the invention. They are obtained by reacting a compound of the formula

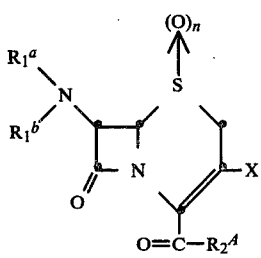

(III)

wherein n is 1 and X is hydroxy, chlorine, bromine or a sulfonyloxy group of the formula —O—SO$_2$—R$_4$ and R$_1^a$, R$_1^b$ and R$_2$ are as defined for formula I, and wherein, if X is hydroxy, R$_2$ cannot be hydroxy, with a primary or secondary amine of the formula H—N(-R$_3^a$)(R$_3^b$), and, if desired, converting a resultant salt into the free compound or into another salt and/or converting a resultant free compound containing a salt-forming group into a salt.

In a sulfonyloxy group of the formula —O—SO$_2$—R$_4$, R$_4$ is an unsubstituted or substituted, in particular aliphatic, cycloaliphatic, araliphatic or aromatic hydrocarbon radical containing up to 18, preferably up to 10, carbon atoms. Suitable groups R$_4$ are e.g. alkyl, preferably lower alkyl such as methyl, ethyl or butyl, or alkenyl such as allyl or butenyl, or cycloalkyl such as cyclopentyl or cyclohexyl, which groups are unsubstituted or mono- or polysubstituted by lower alkoxy such as methoxy, halogen such as fluorine, chlorine or bromine, aryl such as phenyl, or aryloxy such as phenoxy; or naphthyl or, in particular, phenyl groups, which groups are unsubstituted or mono- or polysubstituted by lower alkyl such as methyl, lower alkoxy such as methoxy, halogen such as fluorine, chlorine or bromine, aryl such as phenyl, aryloxy such as phenyloxy, or nitro, for example phenyl, o-, m- or, preferably, p-tolyl, o-, m- or, preferably, p-methoxyphenyl, o-, m- or p-chlorophenyl, p-biphenylyl, p-phenoxyphenyl, p-nitrophenyl, or 1- or 2-naphthyl.

It is preferred to carry out the reaction in a suitable inert polar solvent. Examples of such suitable solvents are unsubstituted or halogenated hydrocarbons, e.g. benzene, toluene, xylene or methylene chloride, ethers, e.g. diethyl ether, lower alkylene glycol di-lower alkyl ethers, e.g. dimethoxy ethane or diethylene glycol dimethyl ether, cyclic ethers, e.g. dioxane or tetrahydrofurane, carboxamides, e.g. dimethyl formamide or lower alkanols, e.g. methanol, ethanol or tert-butanol, or mixtures thereof. If necessary, the reaction is carried out in an inert gas atmosphere, e.g. in an argon or nitrogen atmosphere.

The reaction temperature is in the range from about −20° to +80° C., with the preferred range being from about 0° to 30° C. It is preferred to use 2 to 5 equivalents, and at least an equivalent amount, of primary or secondary amine, based on the starting material of the formula III.

The starting compounds of the formula III are known or they can be prepared in a manner known per se, e.g. by methods similar to those described in German Offenlegungsschrift specification Nos. 2 331 148, 2 506 330 or 2 606 196.

Compounds of the formula I, wherein n is 0, are known or can be prepared in a manner known per se, e.g. as described in German Offenlegungsschrift No. 2 606 196.

Compounds of the formula II can be obtained from compounds of the formula III or by the process described in German Offenlegungsschrift No. 2 606 196 in situ and without isolation, and further processed to compounds of the formula I.

The invention is illustrated by the following Examples, but is in no way restricted to what is described therein.

EXAMPLE 1

5.86 g (10 mmols) of 7β-phenoxyacetylamino-3-morpholino-3-cephem-4-carboxylic acid benzhydryl ester are dissolved in 25 ml of dimethyl formamide and 25 ml of glacial acetic acid. The solution is cooled to 0° C. and then 2.04 g of sodium borohydride are added in 100 mg portions over 1 hour, with vigorous evolution of gas occurring after each addition. The reaction mixture is stirred for further 5 hours at room temperature, then diluted with 300 ml of water and extracted with four 100 ml portions of methylene chloride. After neutralisation with aqueous sodium bicarbonate solution, the organic phase is concentrated in vacuo and the dimethyl formamide is distilled off in a high vacuum. The oily, orange residue is chromatographed on silica gel with toluene/ethyl acetate (96:5), affording pure 7β-phenoxyacetylamino-3-cephem-4-carboxylic acid benzhydryl ester as a white foam.

EXAMPLE 2

A solution of 1.05 g of sodium cyanoborohydride in 30 ml of tetrahydrofurane is added dropwise over 20 minutes to a solution of 5.86 g (10 mmols) of 7β-phenoxyacetylamino-3-morpholino-3-cephem-4-carboxylic acid benzhydryl ester in 50 ml of methylene chloride and 50 ml of glacial acetic acid, whereupon vigorous evolution of gas occurs. Then 20 ml of formic acid are added and the reaction mixture is stirred for 16 hours at room temperature. For working up, the reaction mixture is diluted with 300 ml of methylene chloride and the organic phase is washed four times with 100 ml of water, then dried over sodium sulfate. The solvent is distilled off in vacuo. The almost colourless crude product is chromatographed on silica gel with toluene/ethyl acetate (9:1), affording pure 7β-phenoxyacetylamino-3-cephem-4-carboxylic acid benzhydryl ester.

EXAMPLE 3

4.76 g (20 mmols) of cobalt(II) chloride hexahydrate are added in several portions, at 0°-5° C., to a solution of 11.7 g (20 mmols) of 7β-phenoxyacetylamino-3-piperidino-3-cephem-4-carboxylic acid benzhydryl ester in 50 ml of dimethyl formamide. The solution turns dark blue. Then 75 ml of glacial acetic acid are added dropwise at 0° C. over 30 minutes. Then 4.08 g (120 mmols) of sodium borohydride are added in 200 mg portions over 1 hour, with vigorous evolution of gas after each addition. When the addition is complete, the reaction mixture is warmed to room temperature and, after the addition of a further 50 ml of glacial acetic acid, stirred for 36 hours at room temperature. The dark red solution is filtered to remove the pink precipitate, the filter residue is washed with methylene chloride, and the filtrate is concentrated in vacuo. The dimethyl formamide is distilled off in a high vacuum. The oily residue is dissolved in methylene chloride and washed three times with 50 ml of water. The methylene chloride solution is filtered over 50 g of silica gel to remove residual cobalt salts and the eluate is concentrated, affording pure 7β-phenoxyacetylamino-3-cephem-4-carboxylic acid benzhydryl ester as a white foam.

EXAMPLE 4

11.4 g (20 mmols) of 7β-benzylacetylamino-3-morpholino-3-cephem-4-carboxylic acid benzhydryl ester are dissolved in 50 ml of ethanol, 50 ml of methylene chloride and 50 ml of glacial acetic acid. The solution is cooled to 0° C. and then, with stirring and under nitrogen, 4.08 g (120 mmols) of sodium borohydride are added in 200 mg portions over 1 hour, with vigorous evolution of gas after each addition. When the addition is complete, the reaction mixture is cooled to room temperature and, after addition of a further 50 ml of glacial acetic acid, stirred for 36 hours at room temperature. The clear, almost colourless solution is concentrated in a rotary evaporator and the residue is partitioned between water and methylene chloride. The organic phase is washed again with two 50 ml portions of water and then concentrated in vacuo, affording crude 7β-benzylacetylamino-3-cephem-4-carboxylic acid benzhydryl ester as a foam.

EXAMPLE 5

(a) To a mixture of 9.5 g (50 mmols) of titanium(IV) chloride and 5.67 g (150 mmols) of sodium borohydride in 150 ml of dimethoxy ethane is slowly added, at −20° C., a suspension of 10.86 g (20 mmols) of 7β-[2-(2-thienyl)-acetylamino]-3-pyrrolidino-3-cephem-4-carboxylic acid p-nitrobenzyl ester 1-oxide in 150 ml of ethylene glycol dimethyl ether, so that the temperature does not rise above −15° C. When the addition is complete, the reaction mixture is warmed to 0° C. and then a mixture of 50 ml of glacial acetic acid and 50 ml of ethylene glycol dimethyl ether is added dropwise. The reaction mixture is then stirred for 36 hours at room temperature. While cooling with ice, 200 ml of ice-water are cautiously added dropwise to the blue reaction solution. After extraction with three 150 ml portions of methylene chloride, the organic phase is dried over sodium sulfate and the solvent is removed by vacuum distillation, affording almost pure 7β-[2-(2-thienyl)-acetylamino]-3-cephem-4-carboxylic acid p-nitrobenzyl ester as a foam.

(b) The starting material can be prepared as follows:

To a solution of 19.6 g (40 mmols) of 7β-[2-(2-thienyl)-acetylamino]-3-hydroxy-3-cephem-4-carboxylic acid p-nitrobenzyl ester 1-oxide in 150 ml of methylene chloride are added, at −10° C., 9.2 g (80 mmols) of methanesulfonyl chloride. Then 8.1 g (80 mmols) of triethylamine are added dropwise over 1 hour at −10° C. and stirring is continued for 1 hour at this temperature. Then 8.53 g (120 mmols) of pyrrolidine are added dropwise over 1 hour at −10° C. and, when the addition is complete, the reaction mixture is warmed to 25° C. The organic phase is washed three times with 100 ml of water and concentrated in vacuo. The residue is crystallized from 200 ml of methanol, affording pure 7β-[2-(2-thienylacetylamino]-3-pyrrolidino-3-cephem-4-carboxylic acid p-nitrobenzyl ester 1- oxide.

EXAMPLE 6

While cooling with ice, a solution of 5.4 g (100 mmols) of potassium borohydride in 50 ml of dimethyl formamide is added over 1 hour to a solution of 11.4 g (20 mmols) of 7β-phenoxyacetylamino-3-pyrrolidino-3-cephem-4-carboxylic acid benzhydryl ester in 50 ml of methylene chloride, 50 ml of ethanol and 50 ml of glacial acetic acid. The mixture is then stirred for 36 hours at room temperature, concentrated to half its volume, diluted with ice-water, and extracted several times with methylene chloride. The solvent is then removed by vacuum distillation, affording 7β-phenoxyacetylamino-3-cephem-4-carboxylic acid benzhydryl ester as a white foam.

EXAMPLE 7

(a) A suspension is prepared from 142 g (3.75 mmols) of sodium borohydride and 2.4 liters of abs. toluene and then 2.2 liters of glacial acetic acid are added over 4 hours at 20° C. The hydrogen formed during the exothermic reaction is drawn off. To the triacetoxy borohydride so formed are then added, at 20° C., 400 g (0.683 mmol) of 7β-phenoxyacetylamino-3-morpholino-3-cephem-4-carboxylic acid benzhydryl ester in 1.2 liters of glacial acetic acid and 600 ml of abs. toluene. The reaction mixture is warmed to 40° C. and then stirred for 24 hours at this temperature. The solvent is then removed completely by vacuum distillation and the oily residue is partitioned between 1.4 liters of water and 1.4 liters of toluene. The phases are separated and the aqueous phase is extracted with 600 ml of toluene. The combined organic phases are neutralised with saturated sodium bicarbonate solution and washed with two 50 ml portions of water. The organic phase is concentrated under reduced pressure and the oily residue is dissolved in 1.5 liters of ethanol at 55° C. Inoculation of the slowly cooling solution results in the crystallisation of 7β-phenoxyacetylamino-3-cephem-4-carboxylic acid benzhydryl ester.

(b) To a solution of 20 g (40 mmols) of 7β-phenoxyacetylamino-3-cephem-4-carboxylic acid benzhydryl ester in 400 ml of abs. methylene chloride are added, at −15° C., 38.6 ml (0.48 mmol) of abs. pyridine and 320 ml (0.12 mmol) of an 8% solution of phosphorus pentachloride in abs. methylene chloride. After stirring for 30 minutes at −10° C. and for 30 minutes at −5° C., the yellow solution is cooled to −20° C. and then 270 ml of abs. methanol are added, while ensuring that the temperature does not rise above −10° C. Stirring is continued for 1 hour at −10° C. and for 1 hour at room temperature and then the pH is adjusted to 2 by slowly adding a small amount of potassium dihydrogen phosphate and a few drops of phosphoric acid. The aqueous phase is separated and extracted with two 100 ml portions of methylene chloride. The organic extracts are combined and washed with two 50 ml portions of water and then dried over sodium sulfate. The solvent is removed by distillation and the oily residue is dissolved in 20 ml of ethyl acetate. To the solution is added a solution of 11 g of p-toluenesulfonic acid monohydrate in 150 ml of ethyl acetate. The mixture is evaporated to dryness and the residue is dissolved in methylene chloride. 7β-Amino-3-cephem-4-carboxylic acid benzhydryl ester p-toluenesulfonate is precipitated with ether as a white crystalline solid.

(c) 36.6 g of 7β-amino-3-cephem-4-carboxylic acid benzhydryl ester in 60 ml of anisole are reacted for 10 minutes at room temperature with 240 ml of trifluoroacetic acid. The reaction mixture is diluted with toluene and evaporated to dryness in vacuo. The residue is dissolved in a mixture of 150 ml of methanol, 250 ml of ether and 10 ml of water and the pH is adjusted to 3.5 with triethylamine. The suspension is cooled for 1 hour to 0° C. and the fine-crystalline precipitate of 7β-amino-3-cephem-4-carboxylic acid is isolated by filtration.

(d) 5.02 ml (5.5 mmols) of phosphoroxy chloride are added dropwise to 4.23 ml (5.5 mmols) of dimethyl formamide, such that the temperature does not rise above 40° C. The mixture is cooled to 20° C., diluted with 60 ml of ethyl acetate, then cooled to 0° C. Then 11.46 g (5 mmols) of 2-(2-formylamino-4-thiazolyl)-2-methoximinoacetic acid are added, the temperature rising to 8° C. The clear, pale yellow solution is then stirred for 2 hours at 0° C. In a second reaction vessel, 10 g (5 mmols) of 7$\beta$-amino-3-cephem-4-carboxylic acid are suspended in 60 ml of ethyl acetate and then 15.32 ml (6.25 mmol) of N,O-bis-trimethylsilyl acetamide are added. The mixture is stirred for 30 minutes at room temperature and then cooled to −36° C. The solution with the acid chloride is then added to the 2-(2-formylamino-4-thiazolyl)-2-methoxyiminoacetic acid over 30 minutes, the temperature rising to −3° C. The clear, yellow solution is stirred for 45 minutes at −10° C. and then poured into 400 ml of saturated sodium carbonate solution and the pH is adjusted to 7.8 with further sodium solution. The phases are separated and the aqueous phase is extracted with 200 ml of ethyl acetate and the subsequently extracted organic phase is washed with 10 ml of water. The aqueous phase is adjusted to pH 1.7 with 30 ml of conc. hydrochloride acid and extracted with three 300 ml portions of ethyl acetate. The combined organic phases are washed with two 100 ml portions of saturated sodium chloride solution and dried over sodium sulfate. The organic phase is concentrated to about 400 ml and 7$\beta$-[2-(2-amino-4-thiazolyl)-2-methoximinoacetamido]-3-cephem-4-carboxylic acid crystallises out overnight.

(e) A mixture of 2.25 ml of chloromethyl pivalate and 9 g of sodium iodide in 30 ml of acetone is stirred for 3 hours at room temperature. To the mixture is added a solution of 2.6 g of the sodium salt of 7$\beta$-[2-(2-tert-butoxy-carbonylamino-4-thiazolyl)-2-methoximinoacetamido]-3-cephem-4-carboxylic acid in 50 ml of dimethyl formamide and stirring is continued for 1 hour at room temperature. The mixture is concentrated in vacuo and the residue is dissolved in ethyl acetate. The solution is washed with saturated aqueous sodium chloride solution and dried over sodium sulfate, then concentrated in vacuo. The crude product is chromatographed on silica gel. Elution with toluene containing 25–30% of ethyl acetate gives 7$\beta$-[2-(2-tert-butoxy-carbonylamino-4-thiazolyl)-2-methoximinoacetamido]-3-cephem-4-carboxylic acid pivaloyloxymethyl ester. This ester is dissolved in 8.7 ml of methylene chloride, then 8.7 ml of trifluoroacetic acid are added and the mixture is stirred for 1 hour at room temperature. After addition of cold toluene, the batch is concentrated in vacuo. The residue is stirred in diethyl ether/hexane (1:1) and filtered. The filter residue is dried and the brown powder obtained is taken up in ethyl acetate and the solution is washed with saturated aqueous sodium chloride solution, dried over sodium sulfate and concentrated in vacuo. The residue is digested with diethyl ether, filtered, and the filter residue is dried in a high vacuum. The resultant 7$\beta$-[2-(2-amino-4-thiazolyl)-2-methoximinoacetamido]-3-cephem-4-carboxylic acid pivaloyloxymethyl ester decomposes from about 130° C.

EXAMPLE 8

The compounds of the formula I listed below can be obtained by procedures similar to those described in Examples 1 to 7, starting from the corresponding compounds of formula II and, if desired, after deacylation and acylation at the 7$\beta$-amino group:

7$\beta$-phenyloxyacetylamino-3-cephem-4-carboxylic acid,
7$\beta$-phenylacetylamino-3-cephem-4-carboxylic acid,
7$\beta$-thien-2- or 3-ylacetylamino-3-cephem-4-carboxylic acid,
7$\beta$-fur-2- or 3-ylacetylamino-3-cephem-4-carboxylic acid,
7$\beta$-(5-carboxy-5-aminovalerylamino)-3-cephem-4-carboxylic acid and the tert-butyl, trichloroethyl, benzyl, p-methoxybenzyl, p-nitrobenzyl and diphenylmethyl esters of these compounds;
7$\beta$-[D-2-amino-2-phenylacetylamino]-3-cephem-4-carboxylic acid,
7$\beta$-[D-2-tert-butoxycarbonylamino-2-phenylacetylamino]-3-cephem-4-carboxylic acid tert-butyl ester,
7$\beta$-[D-2-amino-2-(1,4-cyclohexadienyl)-acetylamino]-3-cephem-4-carboxylic acid,
and the trichloroethyl, benzyl, p-methoxyphenyl, p-nitrophenyl and diphenylmethyl esters;
7$\beta$-[D-2-tert-butoxycarbonylamino-2-(1,4-cyclohexadienyl)-acetylamino]-3-cephem-4-carboxylic acid tert-butyl ester, and the trichloroethyl, benzyl, p-methoxyphenyl, p-nitrobenzyl and diphenylmethyl esters;
7$\beta$-[2-(2-amino-4-thiazolyl)-2-methoxyiminoacetylamino]-3-cephem-4-carboxylic acid,
7$\beta$-[2-(2-tert-butoxycarbonylamino-4-thiazolyl)-2-methoxyiminoacetylamino]-3-cephem-4-carboxylic acid tert-butyl ester, and the trichloroethyl, benzyl, p-methoxyphenyl, p-nitrobenzyl and diphenylmethyl esters;
7$\beta$-[2-(5-amino-1,2,4-thiadiazol-3-yl)-2-methoxyiminoacetylamino]-3-cephem-4-carboxylic acid,
7$\beta$-[2-(5-tert-butoxycarbonylamino-1,2,4-thiadiazol-3-yl)-2-methoxyiminoacetylamino]-3-cephem-4-carboxylic acid tert-butyl ester,
and the trichloroethyl, benzyl, p-methoxyphenyl, p-nitrobenzyl and diphenylmethyl esters;
7$\beta$-[2-(5-amino-1,2,4-thiadiazol-3-yl)-2-(carboxyprop-2-yloxyimino)-acetylamino]-3-cephem-4-carboxylic acid,
7$\beta$-[2-(5-tert-butoxycarbonylamino-1,2,4-thiadiazol-3-yl)-2-(carboxyprop-2-yloxyimino)-acetylamino]-3-cephem-4-carboxylic acid tert-butyl ester,
and the trichloroethyl, benzyl, p-methoxyphenyl, p-nitrobenzyl and diphenylmethyl esters;
7$\beta$-[2-(5-amino-1,2,4-thiadiazol-3-yl)-2-hydroxyiminoacetylamino]-3-cephem-4-carboxylic acid,
7$\beta$-[2-(5-tert-butoxycarbonylamino-1,2,4-thiadiazol-3-yl)-2-hydroxyimino-acetylamino]-3-cephem-4-carboxylic acid tert-butyl ester,
and the trichloroethyl, benzyl, p-methoxyphenyl, p-nitrobenzyl and diphenylmethyl esters;
7$\beta$-[2-(5-N-methylamino-1,2,4-thiadiazol-3-yl)-2-Z-methoxyimino-acetylamino]-3-cephem-4-carboxylic acid, and the tert-butyl, trichloroethyl, benzyl, p-methoxyphenyl, p-nitrobenzyl and diphenylmethyl esters;
7$\beta$-amino-3-cephem-4-carboxylic acid,
7$\beta$-amino-3-cephem-4-carboxylic acid tert-butyl ester,
7$\beta$-amino-3-cephem-4-carboxylic acid trichloroethyl ester,
7$\beta$-amino-3-cephem-4-carboxylic acid benzyl ester,
7$\beta$-amino-3-cephem-4-carboxylic acid p-methoxybenzyl ester, 7β-amino-3-cephem-4-carboxylic acid p-nitrobenzyl ester and 7β-amino-3-cephem-4-carboxylic acid diphenylmethyl ester.

In the above compounds, the amino groups in the 7β-acetyl radicals can also be protected by the trichloroethoxycarbonyl group or the chloroacetyl group.

What is claimed is:

1. A process for the production of a 7β-amino-3-cephem-4-carboxylic acid compound of the formula

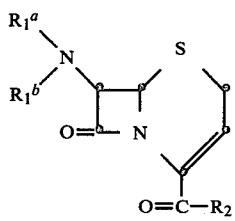

wherein $R_1{}^a$ is hydrogen, an acyl group of the formula:

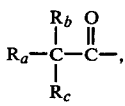

wherein (1) $R_a$ is phenyl, hydroxyphenyl, lower alkylsulfonylaminophenyl, aminomethylphenyl, 2- or 3-thienyl, aminomethylthienyl, furyl, aminomethylfuryl, cyclohexadienyl, aminomethyl-1,4-cyclohexadienyl, cyclohexenyl, aminomethyl-1-cyclohexenyl, aminothiazolyl, lower alkylaminothiazolyl, aminothiadiazolyl, or lower alkylaminothiadiazolyl, in which the hydroxy and amino groups are in the free form or are protected by conventional hydroxy- and amino protecting groups, $R_b$ is hydrogen, and $R_c$ is hydrogen, amino or amino protected by a conventional amino protecting group, hydroxy, hydroxy protected by a conventional hydroxy protecting group, carboxy, lower alkoxycarbonyl, or sulfo, or wherein (2) $R_a$ is 3-amino-3-carboxypropyl or 3-amino-3-carboxypropyl in which amino and carboxy are protected by conventional amino and carboxy protecting groups, cyano, 1-tetrazolyl, phenoxy, or 4-pyridylthio, and $R_b$ and $R_c$ are hydrogen, or wherein (3) $R_a$ is phenyl, thienyl, 2-furyl, 2-amino-4-thiazolyl, 2-lower alkylamino-4-thiazolyl, 5-amino-1,2,4-thiadiazolyl or 5-lower alkylamino-1,2,4-thiadiazolyl wherein amino can be protected by a conventional amino protecting group, and $R_b$ and $R_c$ together are syn-lower alkoximino, or is an amino protective group $R_1{}^A$ selected from the group consisting of trityl, 1-lower alkoxycarbonyl-1-propen-2-yl, 2-nitrophenylthio, pentachlorophenylthio, tritylthio, tri-lower alkylsilyl, halo-lower alkoxy-lower alkylsilyl and tri-lower alkylsilyl, $R_1{}^b$ is hydrogen, or $R_1{}^a$ and $R_1{}^b$ together ar a bivalent amino protecting group selected from the group consisting of succinyl, phthaloyl and 4,4-dimethyl-2-phenyl-1-oxo-3-aza-1,4-butylene, and $R_2$ is hydroxy, or a group which, together with the carbonyl grouping —C(═O)— forms a conventionally protected carboxy group, which comprises reacting a compound of the formula

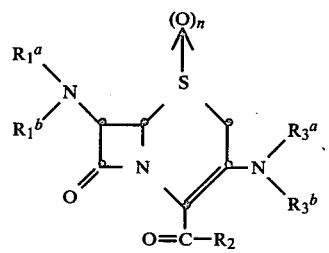

wherein n is 0 or 1, $R_1{}^a$, $R_1{}^b$ and $R_2$ are as defined for formula I, and the group of the formula —N($R_3{}^a$) ($R_3{}^b$) is a secondary amino group wherein one of the groups $R_3{}^a$ and $R_3{}^b$ represents hydrogen and the other lower alkyl, lower alkyl substituted by lower alkoxy, lower alkylthio, cycloalkyl, phenyl or thienyl, cycloalkyl, or cycloalkyl substituted by lower alkoxy or lower alkylthio, or —N($R_3{}^a$) ($R_3{}^b$) represents a tertiary amino group wherein $R_3{}^a$ and $R_3{}^b$ are the same or different and represent lower alkyl, lower alkyl substituted by lower alkoxy, lower alkylthio, cycloalkyl, phenyl or thienyl, cycloalkyl or cycloalkyl substituted by lower alkoxy or lower alkylthio or $R_3{}^a$ and $R_3{}^b$ can be linked with a carbon-carbon bond or with an oxygen or sulfur atom, —NH—, or a lower alkylated nitrogen atom under acid conditions with a complex borohydride.

2. A process according to claim 1 for the production of a compound of formula I wherein $R_1{}^a$ is hydrogen or an acyl group of the formula IA, wherein (1) $R_a$ is phenyl, thienyl, furyl, cyclohexadienyl or cyclohexenyl, thiazolyl or thiadiazolyl substituted by amino, $R_b$ is hydrogen, and $R_c$ is hydrogen, hydroxy, amino, carboxyl or sulfo; or wherein (2) $R_a$ is 3-amino-3-carboxypropyl, cyano, 1-tetrazolyl, or 4-pyridylthio, and $R_b$ and $R_c$ are hydrogen; and wherein (3) $R_a$ is phenyl, thienyl, furyl or thiazolyl or thiadiazolyl substituted by amino and $R_b$ and $R_c$ together are syn-lower alkoxyimino, $R_1{}^b$ is hydrogen, and $R_2$ is hydroxy, tert-butoxy, 2-halo-lower alkoxy, phenacyloxy, 4-methoxybenzyloxy, 4-nitrobenzyloxy, 2-nitro-4,5-dimethoxybenzyloxy, diphenylmethoxy, or 4,4'-dimethoxydiphenylmethoxy.

3. A process according to claim 1 for the production of a compound of the formula I, wherein $R_1{}^a$ is hydrogen or an acyl group of the formula IA, wherein (1) $R_a$ is phenyl, 2- or 3-thienyl, 2- or 3-furyl, $R_b$ is hydrogen, free or conventionally protected amino and $R_c$ is hydrogen; or wherein (2) $R_a$ is phenoxy and each of $R_b$ and $R_c$ is hydrogen; or wherein (3) $R_a$ is phenyl, 2-amino-4-thiazolyl, 2-lower alkylaminothiazolyl, e.g. 2-methylamino-4-thiazolyl, 5-amino-1,2,4-thiadiazolyl or 5-methylamino-1,2,4-thiadiazolyl, wherein amino is in a free form or is protected by lower alkoxycarbonyl or halo-lower alkoxycarbonyl and $R_b$ and $R_c$ together are syn-lower methoximino, and $R_2$ is hydroxy, lower alkoxy, 2-halo-lower alkoxy, nitrobenzyloxy, or diphenylmethoxy.

4. A process according to claim 1 for the production of 7β-phenoxyacetylamino-3-cephem-4-carboxylic acid.

5. A process according to claim 1 for the production of 7β-phenylacetylamino-3-cephem-4-carboxylic acid.

6. A process according to claim 1 for the production of 7β-amino-3-cephem-4-carboxylic acid.

7. A process according to claim 1 for the production of 7β-amino-3-cephem-4-carboxylic acid tert-butyl ester.

8. A process according to claim 1 for the production of 7β-amino-3-cephem-4-carboxylic acid diphenylmethyl ester.

9. A process according to claim 1 for the production of 7β-amino-3-cephem-p-nitrobenzyl ester.

10. A process according to claim 1, wherein an alkali metal borohydride is used as the complex borohydride.

11. A process according to claim 1, wherein sodium borohydride is used as the complex borohydride.

12. A process according to claim 1, wherein potassium borohydride is used as the complex borohydride.

13. A process according to claim 1, wherein sodium cyanoborohydride is used as the complex borohydride.

14. A process according to claim 1, wherein a carboxylic acid, dicarboxylic acid or sulfonic acid is used as acid reagent.

15. A process according to claim 14, wherein glacial acetic acid is used as carboxylic acid.

16. A process according to claim 1, wherein a complex borohydride in the presence of glacial acetic acid is used.

17. A process according to claim 1, wherein a non-oxidising or reducing Lewis acid is used as acid reagent.

18. A process according to claim 17, wherein titanium(IV) chloride is used as Lewis acid.

19. A process according to claim 17, wherein cobalt-(II) chloride is used as Lewis acid.

* * * * *